United States Patent [19]

Inoue et al.

[11] Patent Number: 5,993,625
[45] Date of Patent: Nov. 30, 1999

[54] EXHAUST GAS SENSOR

[75] Inventors: Ryuji Inoue, Gifu; Yumi Kuroki, Aichi; Tomohiro Fuma, Aichi; Shoji Kitanoya, Aichi; Satoshi Sugaya, Aichi; Takafumi Oshima, Aichi, all of Japan

[73] Assignee: NGK Spark Plug Co., Ltd., Nagoya, Japan

[21] Appl. No.: 08/820,522

[22] Filed: Mar. 19, 1997

[30] Foreign Application Priority Data

Mar. 19, 1996 [JP] Japan ........................... 8-90617
Jan. 10, 1997 [JP] Japan ........................... 9-14779

[51] Int. Cl.⁶ .................................................. G01N 27/407
[52] U.S. Cl. ............................. 204/425; 204/426; 422/98
[58] Field of Search ............................. 204/421–429; 422/98

[56] References Cited

U.S. PATENT DOCUMENTS

| H427 | 2/1988 | Hirate et al. | 204/426 |
|---|---|---|---|
| 4,107,019 | 8/1978 | Takao et al. | 204/426 |
| 4,578,172 | 3/1986 | Yamada et al. | 204/426 |
| 4,722,779 | 2/1988 | Yamada et al. | 204/426 |
| 4,765,880 | 8/1988 | Hayakawa et al. | 204/426 |
| 5,250,169 | 10/1993 | Logothetis et al. | 204/424 |
| 5,413,683 | 5/1995 | Murase et al. | 204/426 |
| 5,460,711 | 10/1995 | Riegel et al. | 204/426 |
| 5,474,665 | 12/1995 | Friese et al. | 204/426 |
| 5,476,001 | 12/1995 | Hoetzel et al. | 73/23.31 |
| 5,505,837 | 4/1996 | Friese et al. | 204/425 |
| 5,602,326 | 2/1997 | Takahashi et al. | 73/31.06 |
| 5,672,811 | 9/1997 | Kato et al. | 204/425 |

FOREIGN PATENT DOCUMENTS

| 4 311 849 | 10/1994 | Germany . |
| 4 311 851 | 10/1994 | Germany . |
| 5-180794 | 7/1993 | Japan . |

OTHER PUBLICATIONS

"Journal of the Marine Engine Society", vol. 26, No. 9, pp. 58–62, Sep. 1991.

*Primary Examiner*—T. Tung
*Attorney, Agent, or Firm*—Foley & Lardner

[57] ABSTRACT

In accordance with the present invention, there is provided an exhaust gas sensor which comprises an oxygen pump cell made of solid electrolyte having an oxygen ion conductivity, an oxygen sensor cell made of solid electrolyte having an oxygen ion conductivity and disposed in opposition to the pump cell in such a manner as to define therebetween a detection space, and a semiconductor detection element made of oxide semiconductor and disposed in the detection space for detecting a predetermined detected substance in the exhaust gas introduced to the detection space. The concentration of oxygen in the detection space is regulated so as to be included within a predetermined range through control of charge or discharge of oxygen into or from the detection space by means of the oxygen pump cell on the basis of the concentration of oxygen in the exhaust gas, which is detected by the oxygen sensor cell.

9 Claims, 14 Drawing Sheets

EXHAUST GAS SENSOR

BACKGROUND OF THE INVENTION

1. Field of the Invention

The present invention relates to an exhaust gas sensor or analyzer for detecting contaminants in exhaust gas, such as hydrocarbons (HC), carbon monoxide (CO), oxides of nitrogen ($NO_x$) and the like. The present invention further relates to a method of producing such an exhaust gas sensor. Still further, the present invention relates to a sensor system using such an exhaust gas sensor.

2. Description of the Related Art

It is known to use a resistive type sensor as an analyzer or sensor for detecting the above described contaminants in exhaust gas. In such a sensor, an oxide semiconductor such as a semiconductor made of $SnO_2$ or the like is used as a detection element for detecting the content of contaminants in exhaust gas depending upon a variation in resistance of the oxide semiconductor in proportion to its absorption of contaminants.

The resistive type sensor has such a characteristic that the output of the detection element made of oxide semiconductor varies depending upon a variation of the concentration of oxygen in the exhaust gas. Due to this, there is caused a problem in that the output for detection of the same concentration of contaminants varies depending upon a variation of the concentration of oxygen in the exhaust gas. Thus, as disclosed in Japanese patent provisional publication No. 5-180794, it has been proposed to send oxygen into the exhaust gas by means of a pump cell made of solid electrolyte and make higher the concentration of oxygen therein for thereby making smaller the relative variation in the concentration of oxygen in the exhaust gas and making higher the detection accuracy. However, there still exists a problem in that if the concentration of oxygen in the exhaust gas varies largely, a sufficient restraining effect on restraint of the relative variation in the concentration of oxygen by the effect of introduction of oxygen from the pump cell cannot be obtained and therefore satisfactory detection accuracy cannot be obtained.

SUMMARY OF THE INVENTION

According to an aspect of the present invention, there is provided a novel and improved exhaust gas sensor which includes the following elements:

(1) an oxygen pump cell which is made of solid electrolyte having an oxygen ion conductivity and operative to charge or discharge oxygen into or from a detection space in response to a voltage applied thereto;

(2) an oxygen sensor cell which is made of solid electrolyte having an oxygen ion conductivity and disposed in opposition to the oxygen pump cell so as to define therebetween the detection space while being operative to detect the concentration of oxygen in exhaust gas on the basis of a concentration cell electromotive force resulting from the difference in the concentration of oxygen between the exhaust gas introduced into the detection space and a reference gas; and (3) a semiconductor detection element which is made of oxide semiconductor and disposed in the detection space for detecting a predetermined detected substance in the exhaust gas introduced into the detection space.

The concentration of oxygen in the detection space is regulated so as to be included within a predetermined range through control of the charge or discharge of oxygen by the oxygen pump cell on the basis of the result of detection by the oxygen sensor cell, i.e., on the basis of the detected concentration of oxygen in the exhaust gas, which is detected by the oxygen sensor cell.

In an exhaust gas sensor constructed in the above described manner, the concentration of oxygen in the detection space is detected by the oxygen sensor cell, and on the basis of the detected concentration of oxygen the oxygen pump cell controls charge and discharge of oxygen into and from the detection space for thereby regulating the concentration of oxygen in the detection space. By this, it becomes possible to make the concentration of oxygen in the atmosphere in which a detection element is disposed, be held or maintained within a predetermined range, thus making it possible to detect contaminants in the exhaust gas with higher or improved accuracy. In the meantime, it is desirable to dispose, within the detection space, the semiconductor detection element in a condition of being electrically insulated from the oxygen sensor cell assuredly for improving the accuracy in detection of a detected substance in exhaust gas.

A reference gas introducing space for introducing a reference gas and making it contact the oxygen sensor cell can be formed in the oxygen sensor cell on the side thereof opposite to the detection space for the exhaust gas. In this instance, it becomes possible to apply a voltage to the oxygen sensor cell in such a direction as to make oxygen be conducted or conveyed from the above described detection space side to the reference gas introducing space side so that the oxygen having been conveyed to the reference gas introducing space by way of the oxygen sensor cell constitutes the reference gas. By this, oxygen can be selectively conveyed to the reference gas introducing space by way of the oxygen sensor cell to enable the gas of the concentration of oxygen of nearly 100% to be used as the reference gas, so the accuracy in detection of oxygen by the oxygen sensor cell can be improved.

The oxygen sensor cell can be formed with porous electrodes on the opposite sides opposed in the direction of application of voltage. In this instance, one of the porous electrodes can be formed at a location facing or associated with the reference gas introducing space. In this embodiment, the reference gas introducing space can be communicated with the exhaust gas atmosphere (hereinafter referred to simply as the atmosphere) which is the subject of detection or the open air by way of associated one of the porous electrodes of the oxygen sensor cell and its lead portion. Further, a porous communication portion that crosses the oxygen sensor cell in the thickness direction thereof to communicate at one end thereof with the detection space, can be provided to the oxygen sensor cell to provide communication by way of itself and through the above described porous electrode (and its lead portion) between the reference gas introducing space and the detection space.

In the meantime, in the case of providing communication between the reference gas introducing space with the open air, the above described application of voltage to the oxygen sensor cell is stopped to allow the open air to be introduced into the reference gas introducing space as the reference gas so that the concentration of oxygen in the open air (about 20.95 vol. %) can be used as a fixed concentration point, thus making it possible to simplify the structure of the sensor. In the meantime, in addition to such a porous electrode and its lead portion, an open air communication portion constituted by a groove, etc. can be provided.

In the meantime, in order to make as smaller as possible the influence of a variation of oxygen concentration on the detection of the substance by the semiconductor detection element, it is desirable to set the position at which the detection element is disposed, adjacent the electrodes of the oxygen sensor cell. Further, by disposing the semiconductor detection element on the oxygen sensor cell by interposing therebetween an insulation layer, insulation between the oxygen sensor cell and the semiconductor detection element can be made assuredly.

The kind of oxide semiconductor constituting the semiconductor detection element differs depending upon the kind of detected substance, for example, for detection of CO or HC, $SnO_2$, ZnO, $In_2O_3$ and the like are suitably used. Further, for detection of oxides of nitrogen ($No_x$) $WO_3$, perovskite oxide containing La, and the like can be used suitably. Further, as the solid electrolyte for the oxygen pump cell and the oxygen sensor cell, such $ZrO_2$ base one that is partly stabilized by $Y_2O_3$ or the like can be used suitably.

Then, as the semiconductor detection element, such one that is formed by printing a predetermined element pattern using starting material powder of oxide semiconductor on a previously sintered oxygen sensor cell, and thereafter sintering the printed pattern at the temperature lower than the sintering temperature of the oxygen sensor cell. That is, since the oxide semiconductor used for the semiconductor detection element may, in may cases, sublime or decompose at the sintering temperature of the $ZrO_2$ base solid electrolyte constituting the oxygen sensor cell, it is impossible to form the detection element by simultaneous or concurrent sintering with the oxygen sensor cell. However, as mentioned above, by printing an oxygen sensor cell pattern on the previously sintered oxygen sensor cell and secondarily sintering the printed pattern at a lower temperature, the detection element can be formed readily and assuredly.

Then, the above described exhaust gas sensor can be comprised of an oxygen pump cell unit including an oxygen pump cell and a sensor cell unit including an oxygen sensor cell which are formed so as to constitute separate units and then joined with cement or adhesive to constitute an integral unit. Since with this structure the pump cell unit and the sensor cell unit are formed separately, there results an advantage in being capable of producing the sensor more reasonably, for example, the semiconductor detection element can be formed on the sensor cell unit by secondary sintering and thereafter joined with the pump cell unit to constitute an integral body or unit.

In the above structure, the pump cell unit can have the pump cell side coupling portion, while the sensor cell unit can have the sensor cell side coupling portion to be coupled with the pump cell side coupling portion, so that the pump cell unit and the sensor cell unit can be joined at the coupling portions thereof to constitute an integral body or unit. Such joining can be attained by filling the gap between the coupling portions (hereinafter referred to as coupling gap) with adhesive such as glass or the like. By this, positioning of the pump cell unit and the sensor cell unit for their lamination or piling up can be attained with ease, and in addition the coupling portions can be formed so as to prevent the adhesive such as glass or the like filled in the gap from flowing freely, whereby such a trouble, for example, in that the adhesive is adhered to the semiconductor detection element, the electrodes of the oxygen sensor cell or the oxygen pump cell, etc., is hard to occur. In the meantime, at an intermediate portion of the coupling gap or at a portion of the coupling gap adjacent the open end thereof on the sensor surface side, an adhesive storing portion can be formed in such a manner as to make the coupling gap wider.

By doing so, when the adhesive of the amount more than necessitated is filled in the gap, the excess adhesive can be drawn to the above described storing portion, thus making it possible to prevent occurrence of the above described kind of trouble and the like more assuredly.

The oxygen pump cell unit can be comprised of the following elements:

(1) an oxygen pump cell in the form of an elongated plate;

(2) a detection space forming member formed into an elongated plate corresponding to that of the oxygen pump cell, and placed on one side surface of the oxygen pump cell and joined together therewith, while being formed with a window for forming a detection space, at one of longitudinally separated side portions, in such a manner as to extend in the thickness direction therethrough;

(3) a pair of coupling projections disposed on the side of the detection space forming member opposite to the oxygen pump cell and formed integral with and along opposite ends of the detection space forming member opposed widthwise thereof.

Further, the sensor cell unit can be comprised of the following elements:

(1) an oxygen sensor cell in the form of an elongated plate narrower than the detection space forming member; and (2) a base member formed wider than the oxygen sensor cell and placed on the side of the oxygen sensor cell opposite to the detection space forming member in such a manner as to have opposite end portions that protrude widthwise from the oxygen sensor cell.

The stepped surface portions are constituted by the protruded opposite ends of the base member and the side surface of the oxygen sensor cell to serve as the coupling portion of the oxygen sensor cell unit, and the coupling projections constituting the coupling portion of the pump cell unit are coupled with the stepped surface portions, whereby the pump cell unit and the sensor cell unit are placed one upon another to constitute an integral body or unit.

With the above structure, it becomes possible to form the powder compact for the pump cell unit and sensor cell unit by first splitting it into compact elements in the form of plate or sheet and then placing the elements one upon another to constitute an integral body or unit, whereby the sensor can be produced with efficiency.

Then, each electrodes of the oxygen pump cell and oxygen sensor cell need to have a reversible catalytic function for a dissociation reaction for charging oxygen to the solid electrolyte constituting such cells and an oxygen recombining reaction for allowing oxygen to be discharged from the solid electrolyte (hereinafter referred to as oxygen dissociating and catalyzing function), and such electrodes can be constituted by porous electrodes made of Pt or its alloy for instance.

On the other hand, there may be such a case in which the above described electrode has, depending upon the material from which it is formed and depending upon the detected substance, a catalytic function for a reaction of combining the detected substance and oxygen (i.e., the oxidation reaction or burning reaction of the detected substance) in addition to the oxygen dissociating and catalyzing function. Accordingly, when the electrode located on the side to face or to be associated with the detection space has such an oxidation catalytic function, such a case may occur in which the detected substance is reacted with oxygen in the detection space to be consumed, thus lowering the accuracy in detection of the detected substance by the semiconductor detection element. Thus, by constructing at least those of the electrodes of the pump cell unit and the sensor cell unit that face or that are associated with the above described detection space (hereinafter referred to as detection space side electrode), so as to be catalytically inactive in the reaction of the detected substance and oxygen, it becomes possible to prevent or restrain the detected substance from being reacted with oxygen and consumed, thus making it possible to detect the detected substance with high accuracy by means of the semiconductor element.

In the meantime, the "catalytically inactive electrode in the reaction of the detected substance and oxygen" so referred to in the specification, is such an electrode, if subjected to such a test under a condition in which an example is prepared to have a disk-shaped electrode of 8 mm in diameter which is formed on a solid electrolyte plate of 12 mm in diameter and 1 mm thick and disposed within a tubular body having a gas inlet and outlet and a test gas containing 350 ppm of the detected substance and 300 ppm of oxygen in the argon gas carrier is introduced at the flow rate of 100 ml/min. into the tubular body through the inlet and discharged through the outlet, that causes the concentration of the detected substance in the test gas to reduce to 10% or less. In the meantime, the example is heated up to a predetermined temperature corresponding to the operating temperature of the sensor by means of a heating means such as a heater and the like.

In the meantime, one of the electrodes of the pump cell unit or the oxygen sensor cell which is located on the side not to face be associated with the detection space, can be constructed so as to be catalytically inactive in the reaction of the detected substance and oxygen, provided that it has a sufficient oxygen dissociating and catalyzing function for operating the pump cell unit or the oxygen sensor cell.

The above described detection space side electrode, i.e., at least a portion thereof including a surface for contact with the exhaust gas can be made of a material which is catalytically Inactive in the reaction of the detected substance and oxygen. In this case, it is a matter of course that the entire electrode can be made of the above described catalytically inactive material, but it will do that only the surface of the portion for contact with the exhaust gas is made of a catalytically inactive material, for example, the electrode can be produced by forming a main body from a catalytically active material and providing the surface of the main body with a coating of a catalytically inactive material.

In this connection, what kind of material can be used for a catalytically inactive electrode differs depending upon the operating temperature of the sensor and the kind of the detected substance. For example, the metal containing Au or Ag for its major component is particularly low in its catalytic activity for oxide reaction of CO or HC when CO or HC is the detected substance and has a sufficient oxygen dissociating and catalyzing function, so when this kind of metal is used for the above described electrode material excellent operation of the pump cell unit and the sensor cell unit can be obtained and in addition the above described detected substances can be detected with high accuracy. Further, the electrode formed by the use of the above metal is particularly low in the catalytic activity in the reaction of methane and oxygen and thus has an advantage of being capable of detecting the methane in the exhaust gas selectively.

According to a further aspect of the present invention, there is provided a sensor system which comprises the above described exhaust gas sensor, and oxygen concentration control means for controlling the concentration of oxygen in the detection space so as to be included within a predetermined range through control of charge or discharge of oxygen into or from the detection space by means of the oxygen pump cell through variable control of a voltage to be applied to the oxygen pump cell on the basis of the concentration of oxygen in the exhaust gas, which is detected by the oxygen sensor cell.

The above structure can solve the above noted problems inherent in the prior art device.

It is accordingly an object of the present invention to provide a novel and improved exhaust gas sensor which can detect the concentration of the contaminants contained in the exhaust gas with improved accuracy.

It is a further object of the present invention to provide a novel and improved exhaust gas sensor of the foregoing character which can control the concentration of oxygen in the atmosphere in which a detection element is disposed, so as to be maintained within a predetermined range.

It is a further object of the present invention to provide a method of producing an exhaust gas sensor of the foregoing character.

It is a further object of the present invention to provide a provide a novel and improved sensor system which includes an exhaust gas sensor of the foregoing character.

DETAILED DESCRIPTION OF THE PREFERRED EMBODIMENTS

Figure 1A:
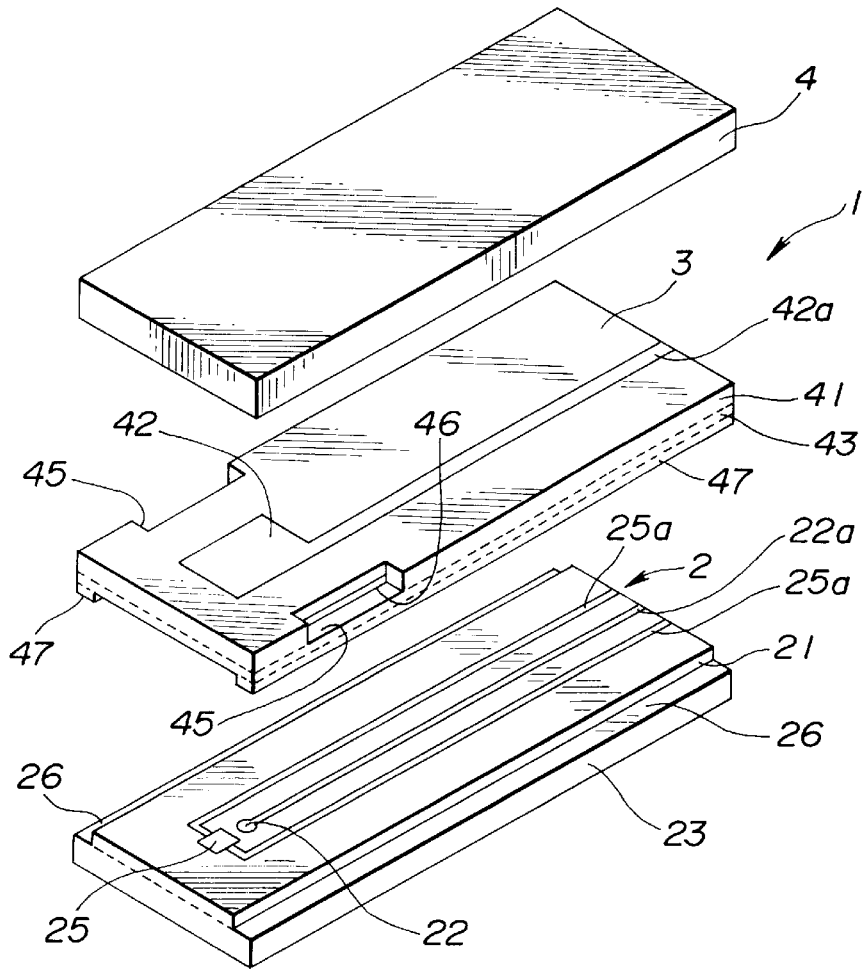
FIG. 1A is an exploded perspective view of an exhaust gas sensor according to an embodiment of the present invention.
Figure 1B:
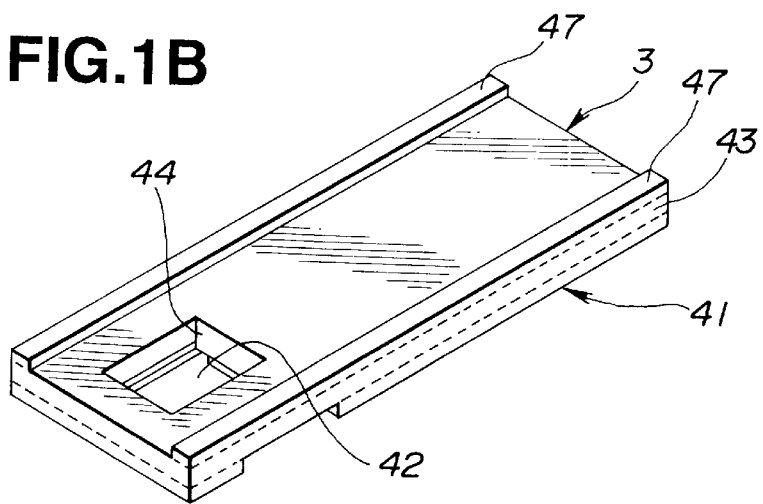
FIG. 1B is a perspective view of a pump cell unit of the exhaust gas sensor of FIG. 1A and shows its side opposite to that shown in FIG. 1A.

Referring first to FIGS. 1A and 1B, an exhaust gas sensor 1 according to an embodiment of the present invention consists of a sensor cell unit 2, a pump cell unit 3 and a heater unit 4 which are in the form of a generally rectangular plate and laminated or placed one upon another in this order to constitute an integral body or unit. The sensor unit 2 has incorporated therein an oxygen sensor cell 21 in the form of a rectangular plate. The oxygen sensor cell 21 has porous electrodes 22 in the place adjacent a longitudinal end and on the opposite side surfaces thereof. The pump cell unit 3 has incorporated therein a similar pump cell 41 having similar porous electrodes 42. In the meantime, the heater unit 4 is constituted by a known ceramic heater or the like.

The oxygen sensor cell 21 and oxygen pump cell 41 are made of solid electrolyte having an oxygen ion conductivity. A typical example of such solid electrolyte is $ZrO_2$ having solid solution of $Y_2O_3$ or $CaO$, but a solid solution of another alkaline earth metal or an oxide of rare earth metal and a solid solution of $Zro_2$ can be used. In this connection, $ZrO_2$, which serves as a base metal, may contain $HfO_2$.

The porous electrodes 22 and 42 of the both cells 2 and 3 have a reversible catalytic function (i.e., oxygen dissociating and catalyzing function) for a dissociation reaction for charging oxygen into the solid electrolyte constituting those cells and an oxygen recombining reaction for allowing oxygen to be discharged from the solid electrolyte, and all of them may be, for example, constructed of Pt porous electrodes. However, in this embodiment, those of the porous electrodes 22 and 42 facing or associated with a detection space 44 are constructed of Pt porous electrodes, and those located on the opposite sides are constructed of Au porous electrodes, respectively. In the meantime, the Au porous electrode is of the kind having a sufficient oxygen dissociating and catalyzing function for activating the oxygen sensor cell 21 and the oxygen pump cell 41, while having a character of being catalytically inactive for the reaction of a detected substance such as methane and oxygen.

As seen from FIG. 1B which is a perspective view taken from the side opposite to that from which FIG. 1A is taken, the oxygen pump cell 41 is joined, at the side opposite to the sensor cell unit 2, with a detection space forming member 43 which is made of the same solid electrolyte as the oxygen pump cell 41 and in the form of a rectangular plate, while being formed with a window at a portion corresponding to the porous electrode 42, to constitute an integral body or unit. The window constitutes the detection space 44. Further, the detection space forming member 43 serves as a reinforcement for reinforcing the oxygen pump cell 41 to prevent or restrain bending and expansion thereof.

Figure 3A:
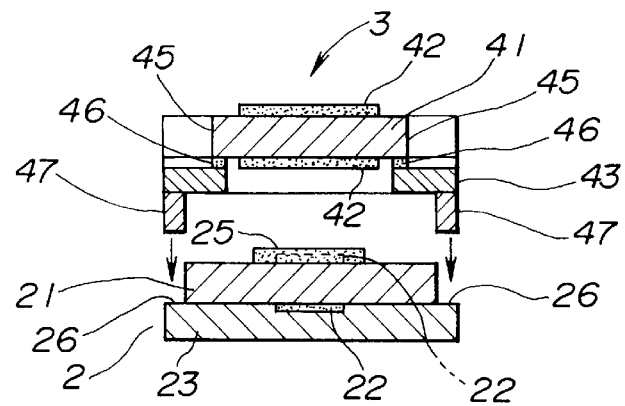
FIG. 3A is an illustration of a process of joining a pump cell unit and a sensor cell unit of the exhaust gas sensor of FIG. 1A.

Further, an electrode lead 42a is formed on the oxygen pump cell 41 so as to protrude from each porous electrodes 42 toward a longitudinal end of the oxygen pump cell 41 (i.e., an attaching end of the sensor 1), so that the electrode lead 42a is to be connected at the attaching end to an external output lead wire or the like. Further, the oxygen pump cell 41 has at opposite ends opposed widthwise thereof and at a location corresponding to the detection space 44 a cut or notched portion 45. As shown in FIG. 3A, a porous ceramic member 46 made of $Al_2O_3$ or the like and having a number of communication pores is disposed at the notched portion 45 and between the oxygen pump cell 41 and the detection space forming member 43 and constructed so as to introduce therethrough exhaust gas into the detection space 44. By this, the soot and oil contained in the exhaust gas becomes hard to intrude into the detection space 44, so it becomes possible to prevent deterioration of the porous electrodes 22 and 42 associated with the detection space 44, resulting from sticking of the above described contaminants thereto. In the meantime, without forming) such a notched potion 45, the porous ceramic member 46 may be disposed between the oxygen pump cell 41 and the detection space forming member 43.

Then, in the sensor cell unit 2, a base member 23 is joined to the oxygen sensor cell 21 in such a way as to contact the side surface thereof opposite to the detention space forming member 43, to constitute an integral body or unit. The base member 23 is formed wider than the oxygen sensor cell 21 and protruded widthwise from the opposite ends of the oxygen sensor cell 21. Further, as shown in FIG. 2C, the porous electrode 22 on the side of the oxygen sensor cell 21 confronting the base member 23 is buried or embedded in the base member 23 so that a reference gas is held or stored in the pores or vacant portion of the porous electrode 22. Accordingly, the vacant portion of the porous electrode 22 can be regarded as constituting a reference gasointroducing space. Further, as shown in FIGS. 1A and 1B, the porous electrode 22 has an integral lead portion 22a, and the above described vacant portion, i.e., the reference gas introducing space of the porous electrode 22 embedded in the base member 23 is communicated by way of the lead portion 22a and at the attaching end of the sensor 1 with the open air. In the meantime, as shown in FIG. 2D, a porous communication portion 21a made of porous zirconia, porous alumina or the like, may be provided across the oxygen sensor cell 21 in the thickness direction and have an end communicated with the detection space 44, so as to provide communication between the reference gas introducing space and the detection space 44 by way of the porous communication portion 21a and the lead portion 22a.

Then, the side of the oxygen sensor cell 21 to be joined with the pump cell unit 3 is covered, at least at a portion formed with a semiconductor detection element 25 and except for an area formed with the porous electrode 22, by an insulation layer 28 (refer to FIGS. 8B) made of $Al_2O_3$ or the like, and the semiconductor detection element 25 in the form of film is formed on the insulation layer 28 at a location adjacent the porous electrode 22. The semiconductor detection element 25 is constituted by oxide semiconductor and detects the concentration of a contaminant (detected substance) on the basis of a variation in the electric resistance thereof in proportion to its absorption of the contaminants which are contained in the exhaust gas introduced into the detection space 44. The kind of oxide semiconductor differs depending upon the kind of detected substance, for example, for detection of CO or HC, $SnO_2$, $ZnO$, $In_2O_3$ and the like are used. Further, for detection of oxides of nitrogen ($NO_x$), $WO_3$ is used.

Figure 2A:
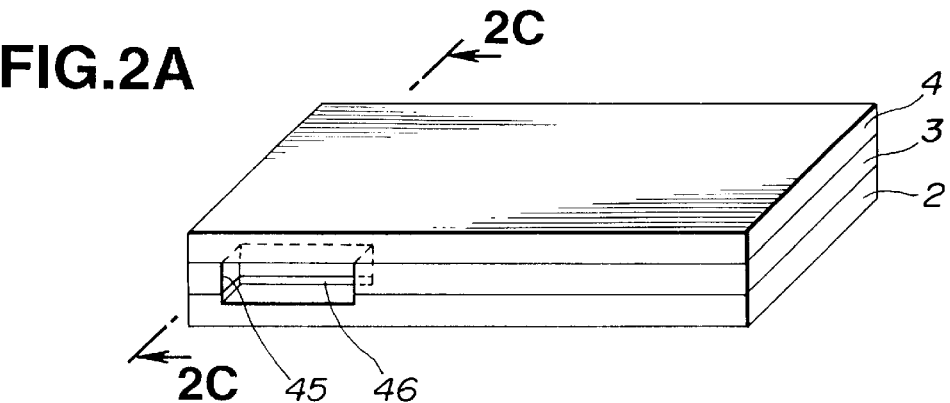
FIG. 2A is a perspective view of the exhaust gas sensor of FIG. 1, in an assembled state.
Figure 2B:
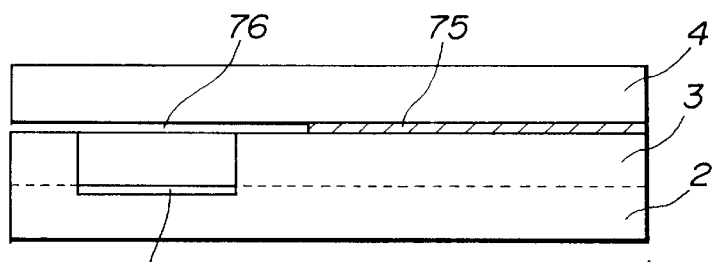
FIG. 2B is an enlarged, side elevation view of the exhaust gas sensor of FIG. 2A.
Figure 2C:
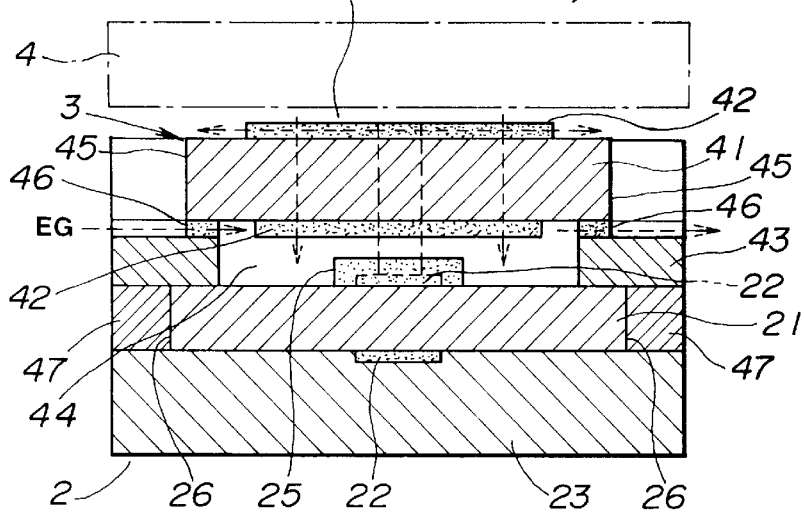
FIG. 2C is a sectional view taken along the line 2C—2C in FIG. 2A.
Figure 3B:
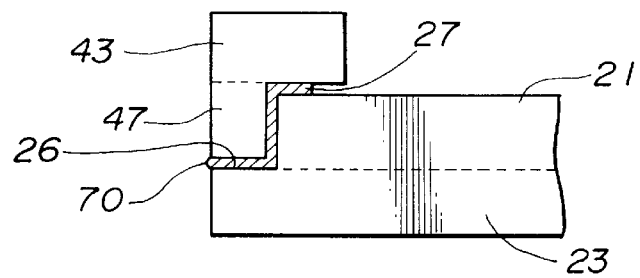
FIGS. 3B and 3C are enlarged fragmentary views of the pump cell unit and sensor cell unit of FIG. 3A, in an assembled state.

As shown in FIG. 2C, the pump cell unit 3 is provided with a pair of coupling projections 47 which are made of the same solid electrolyte as the oxygen pump cell 41 to serve as a pump cell side coupling portion. The coupling projections 47 are disposed along the opposite ends of the oxygen pump cell 41 opposed widthwise and joined with the same to constitute an integral body or unit. On the other hand, in the sensor cell unit 2, a stepped surface formed by the opposite end portions of the base member 23 and the peripheral surface or edge of the oxygen sensor cell 21, serves as or constitute a sensor cell side coupling portion 26. As shown in FIG. 3A, by joining the coupling projection 47 of the pump cell unit 3 to the sensor cell side coupling portion 26, the pump cell unit 3 and the sensor cell unit 2 are joined together to constitute an integral body or unit. In this instance, as shown in FIG. 3B, a clearance or gap formed between the coupling projection 47 and the sensor cell side coupling portion 26 is filled with adhesive such as glass, cement or the like, and the both units 2 and 3 are joined by way of the adhesive 27.

Figure 3C:
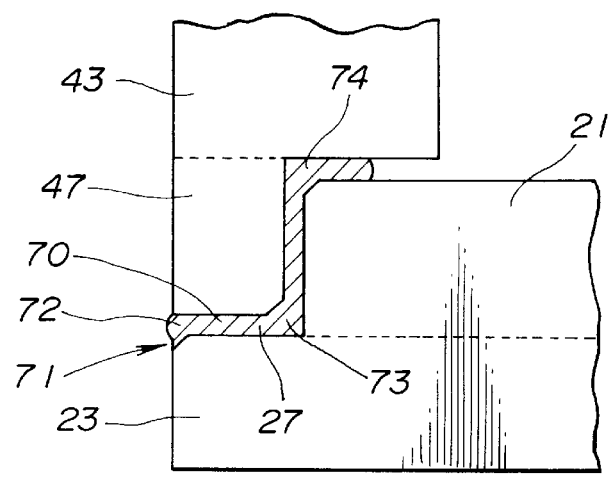

In this connection, as shown in FIG. 3C, adhesive collecting portions 72, 73 and 74 may be formed by partially increasing the clearance 70 at an opening portion 71 opening to the surface of the sensor and the corner portions. More specifically, the collecting portions 72, 73 and 74 are formed by chamfering the base member 23, the corner of the coupling projection 47, and the corner of the oxygen sensor cell 21, respectively. By this, an excess of adhesive is collected at the adhesive collecting portions 72, 73 and 74, so such a trouble in that the adhesive leaks or oozes out from the clearance 70 and sticks to the semiconductor detection element 25 is hard to occur.

In the meantime, since the porous electrodes 22 and 42 of the both units 2 and 3 are brought in direct contact with the exhaust gas except one that constitutes the reference gas introducing space, it is desirable to cover them with a porous protective film made of $Al_2O_3$, spinel, $ZrO_2$, mullite or the like.

Hereinafter, the method of producing the exhaust gas sensor 1 will be described more in detail.

Figure 4:
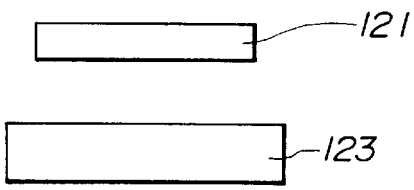
FIG. 4 is a schematic view of compacts for the sensor cell unit of the exhaust gas sensor of FIG. 1A.
Figure 5A:
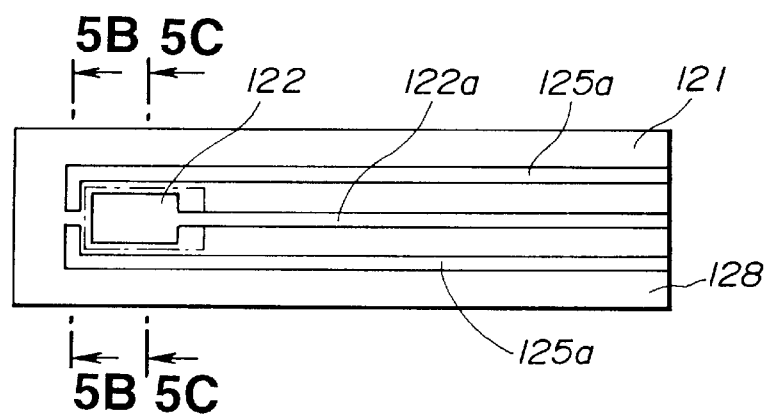
FIG. 5A is a plan view of a compact for an oxygen sensor cell of the sensor cell unit of FIG. 4.
Figure 5B:
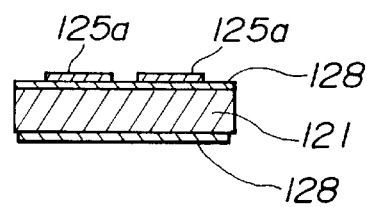
FIG. 5B is a sectional view taken along the line 5B—5B of FIG. 5A.

Firstly, to produce the sensor cell unit 2, a green compact 121 corresponding in shape to the oxygen sensor cell 21 (hereinafter referred to as an oxygen sensor cell compact) and a base member compact 123 are prepared separately as shown in FIG. 4, by using a green sheet which is prepared by mixing solid electrolyte powder with binder. FIG. 5 shows the oxygen sensor cell compact 121 which is formed with an electrode pattern 122 and lead pattern 122a on the side surface thereof to face or to be associated with the detection space 44. Though not shown in FIGS. 5A and 5B, the compact 121 is further formed with an electrode pattern 122 and lead pattern 122a on the side surface thereof to face or contact the base member compact 123. These patterns are produced by printing of a paste which is prepared by mixing Pt or Au powder selected depending upon the electrode material with a predetermined amount (e.g., 10 wt. % or so) of ceramic powder which is of the same material as solid electrolyte, and the printed patterns are respectively formed into the porous electrode 22 and the lead portion 22a by firing (refer to FIG. 1).

Figure 5C:
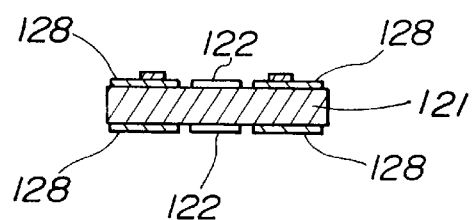
FIG. 5C is a sectional view taken along the line 5C—5C of FIG. 5A.
Figure 6:
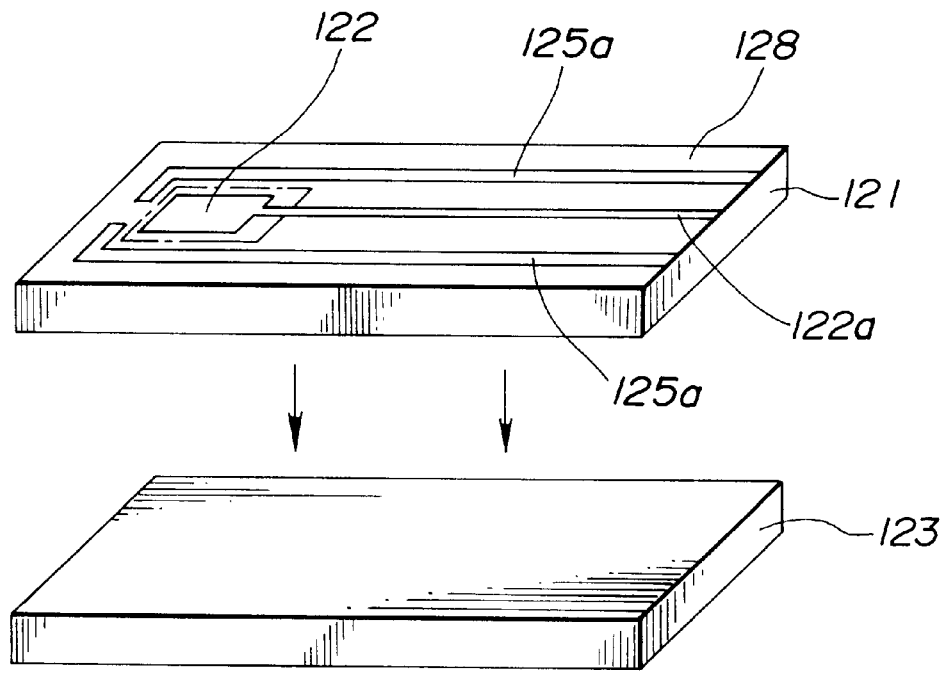
FIG. 6 is an illustration of a process of laminating the compacts for the sensor cell unit of FIG. 4.
Figure 7:
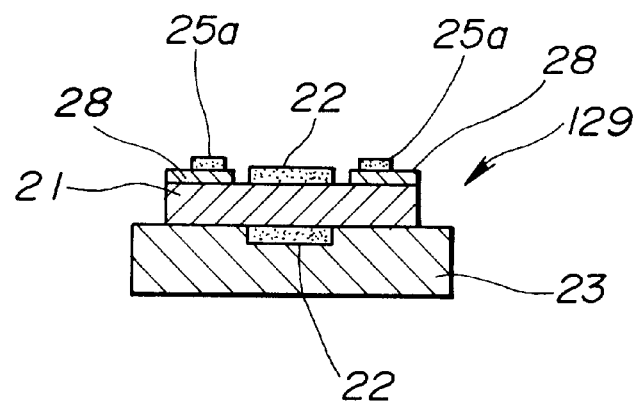
FIG. 7 is a sectional view of a sintered body for the sensor cell unit of the exhaust gas sensor of FIG. 1A, which is obtained by firing the compact assembly of FIG. 6.

Then, as shown in FIGS. 5B and 5C, the side surfaces of the oxygen sensor cell compact 121 are covered by insulation substance layers 128 (formed into the above described insulation layers 28 after firing) except for an area corresponding to the printed patterns 122 for the porous electrodes, and then lead patterns 125a for forming the lead portions 25a (refer to FIG. 1) of the semiconductor detection element 25 are formed on the insulation substance layer 128. As shown in FIG. 6, the base member compact 123 and the oxygen sensor cell compact 121 are placed one upon another and then fired at a predetermined temperature (for example, 1400° C.~1600° C.), whereby the both are joined together and a sintered body 129 as shown in FIG. 7 is obtained. In the meantime, FIG. 7 is a sectional view corresponding to that taken along the line 5C—5C in FIG. 5A.

Figure 8A:
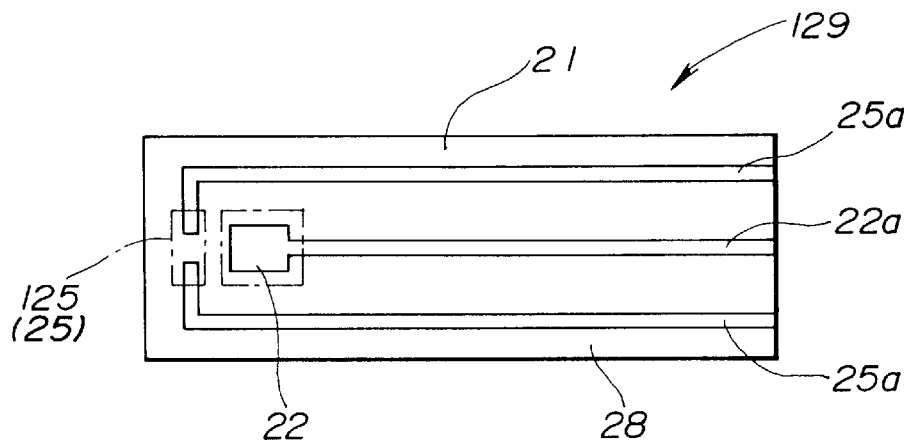
FIGS. 8A and 8B are illustrations of process steps for forming a semiconductor detection element on the sintered body of FIG. 7.
Figure 8B:
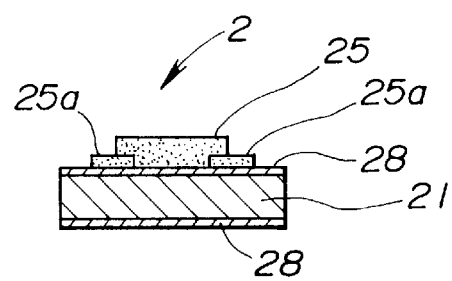

Then, as shown in FIG. 8A, an element pattern 125 is formed on the sintered body 129 by using a paste containing starting material powder of oxide semiconductor and by being printed on the insulation layer 28 in such a manner as to connect between the respective ends of the two lead portions 25a, and then the sintered body 129 is secondarily sintered at the temperature lower than the sintering temperature of the oxygen sensor cell compact 121, whereby the semiconductor detection element 25 as shown in FIG. 8B is obtained. The secondary sintering temperature varies depending upon variations of the material of the oxide semiconductor, e.g., in case of $SnO_2$ it is set so as to be within the range from 900° C. to 1200° C. When the secondary sintering temperature exceeds beyond 1200° C., volatilization of $SnO_2$ during sintering becomes prominent, so it is disabled to form a good detection element 25. On the other hand, in case of 900° C. or less, the adherence (joining strength) between the element and oxygen sensor cell becomes insufficient. In the meantime, in case of $SnO_2$, it is preferable to set the secondary sintering temperature to be within the range from 900° C. to 1000° C.

Figure 9:
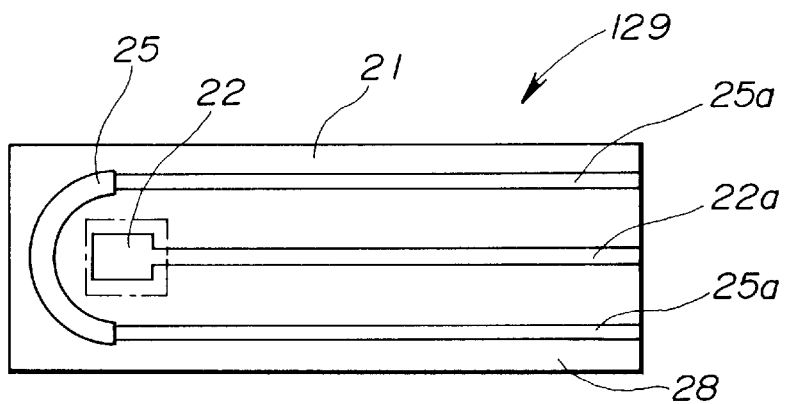
FIG. 9 is a plan view of a variant of the semiconductor detection element of FIGS. 8A and 8B.

In the meantime, though the semiconductor detection element 25 is shown in FIG. 8A as being formed into a rectangular shape, it can otherwise be formed into an arcuate shape surrounding at least a portion of the porous electrode 22 as shown in FIG. 9.

Figure 10:
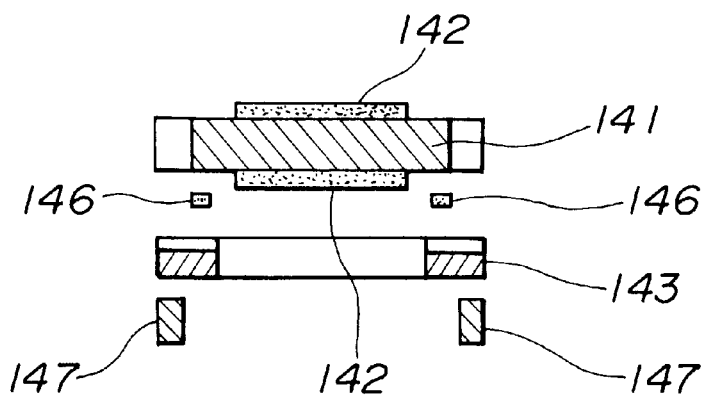
FIG. 10 is a schematic view of compacts for a pump cell unit of the exhaust gas sensor of FIG. 1A.
Figure 11:
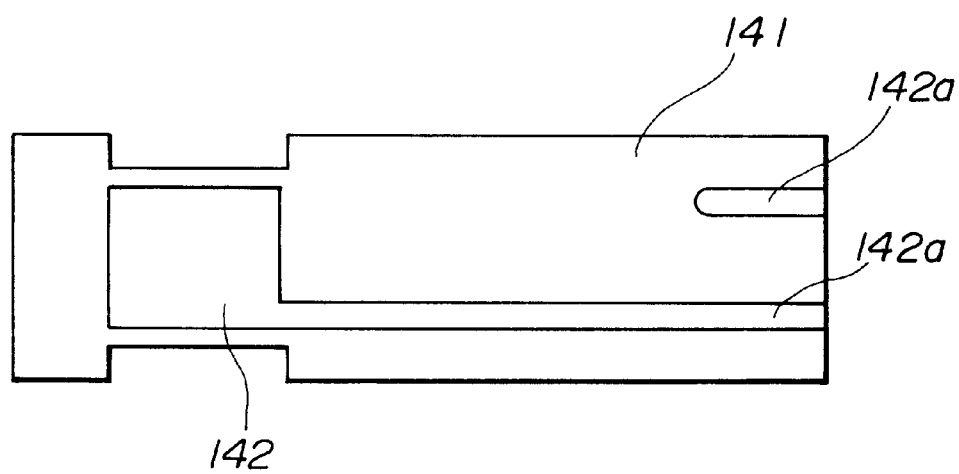
FIG. 11 is a plan view of a compact for an oxygen pump cell, which is one of the compacts of FIG. 10.

The pump cell unit 3 is formed similarly to the sensor cell unit 2. That is, as shown in FIG. 10, compacts 141, 143, 146 and 147 for forming the oxygen pump cell 41, detection space forming member 43, porous ceramic member 46, and coupling projections 47 are prepared independently. Further, as seem from in FIGS. 10 and 11, electrode patterns 142 and lead patterns 142a for forming the electrodes 42 and lead portions 42a are formed on the opposite sides of the compact 141 by printing.

Figure 12A:
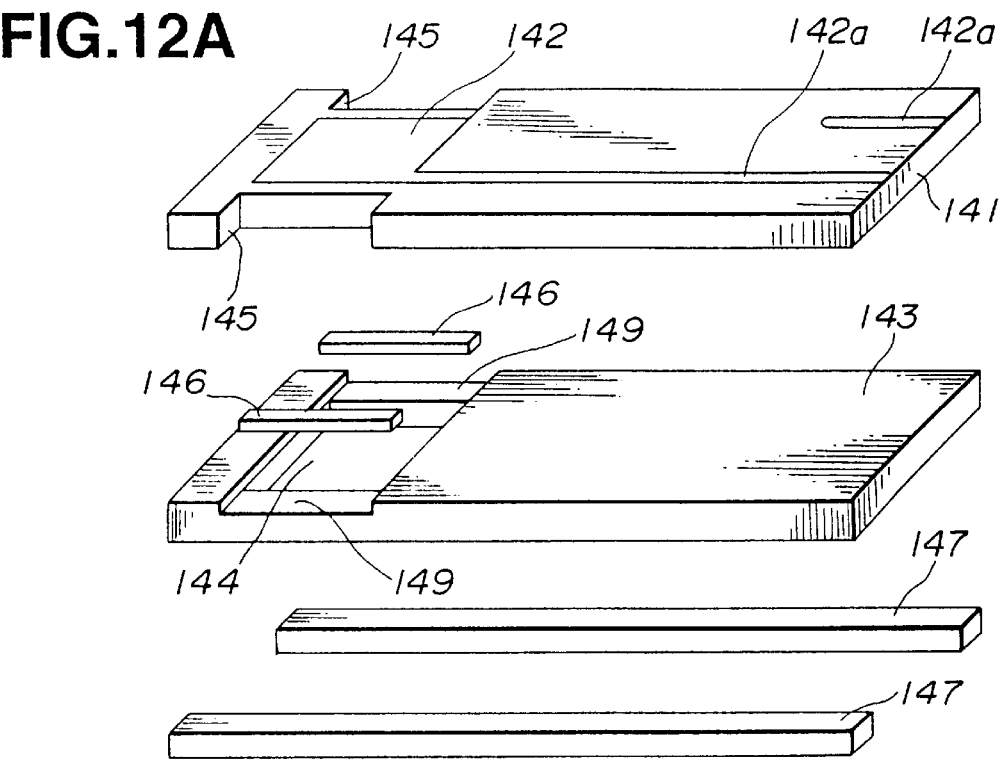
FIG. 12A is an illustration of a process of laminating or piling up the compacts of FIG. 10.
Figure 12B:
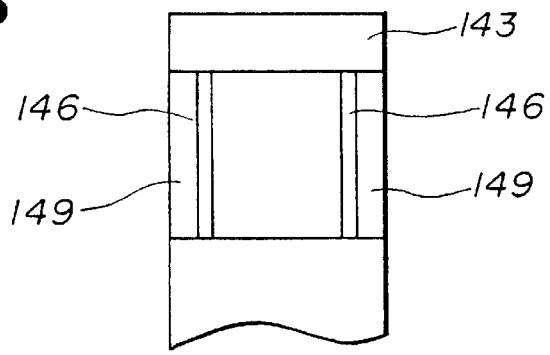
FIG. 12B is a fragmentary plan view of one of the compacts of FIG. 12A.
Figure 13:
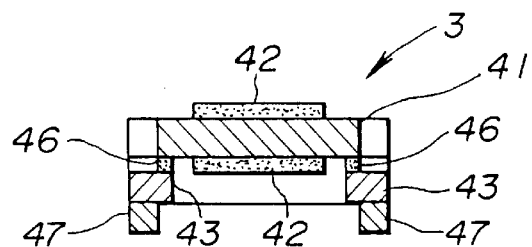
FIG. 13 is a sectional, reduced in scale, view of a sintered body obtained by firing the compact assembly of FIG. 12A.

The above described compacts 141, 143, 146 and 147 are placed one upon another in a positional relationship as shown in FIG. 12A, i.e., the compact 143 for the detection space forming member 43 is disposed in such a manner as to allow the electrode pattern 142 of the compact 141 for the oxygen pump cell 41 to be superimposed on the window portion 144 which defines the detection space 44 after firing, and further the compacts 147 for forming the coupling projections 47 are disposed along the respective edges of the compacts 143 opposed widthwise. Further, the compact 143 is formed with recesses 149 at a location corresponding to the notched portions 145 of the compact 141 which is formed into notched portions 45 after firing and in such a manner as to allow the opposite ends of the window portion 144 of the compact 143 to be recessed in the thickness direction thereof, and as shown in FIG. 12B the compacts 146 for forming the porous ceramic members 46 are fitted in the recesses 149. This laminated assembly is fired at a temperature within the range similar to that of the sensor cell unit, whereby the laminated sections of the assembly are joined together to constitute the pump cell unit 3 as shown in FIG. 13.

The sensor cell unit 2 and the pump cell unit 3 which are formed in the above manner are adhered by the adhesive 27 as shown in FIG. 3 to constitute an integral body or unit. In the meantime, since the fluidity of the adhesive 27 made of glass or the like is relatively large, it is desirable, for the purpose of making it hard to occur that the adhesive leaks off and sticks to the semiconductor detection element 25 and the lead portion 25a (refer to FIG. 1), to allow the adhesive to be filled mainly at a location adjacent the peripheral surface of the pump cell 21, and it is further desirable to form one of such adhesive collecting portions 72, 73 an 74 as shown in FIG. 3C.

Figure 2D:
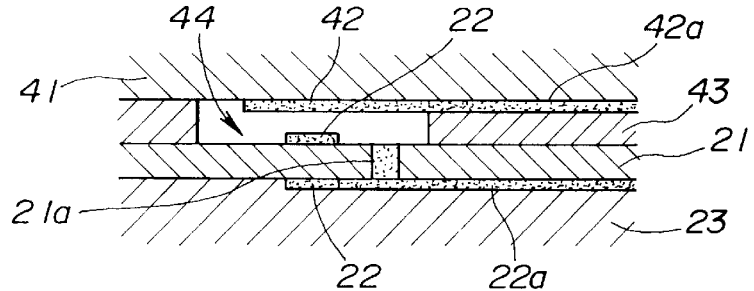
FIG. 2D is a view similar to FIG. 2C but shows fragmentarily a variant of the present invention.

As shown in FIG. 2A, the heater unit 4 is similarly adhered to the above described pump cell unit 3 by an adhesive such as glass or the like, to constitute the exhaust gas sensor 1. In this instance, a resistance type heating element is buried or embedded in the heater unit 4 at a portion thereof corresponding in position to the detection space 44 so that the temperature of the heater unit 4 rises easily or readily particularly at or adjacent that portion. Thus, as shown in FIG. 2B, it is desirable to join the pump cell unit 3 and the heater unit 4 at the base end or attaching end side thereof with the adhesive 75 without filling the adhesive 75 into the side where the detection space 44 is located and the heater unit 4 gives off high temperature heat. Further, by doing so, the adhesive 75 is less likely to stick to the porous electrode 42, the semiconductor detection element 25 or the like within the detection space 44. In addition, by not filling the adhesive 75 in the above described manner, a clearance 76 is formed between the pump cell unit 3 and the heater unit 4, so it becomes possible to allow the exhaust gas EG in the atmosphere to contact the porous electrode 42 on the opposite side of the detection space smoothly.

In the meantime, in FIGS. 1 to 3, the insulation layers 28 are omitted for brevity.

Hereinafter, description will be made as to how to use the exhaust gas sensor 1.

Figure 14:
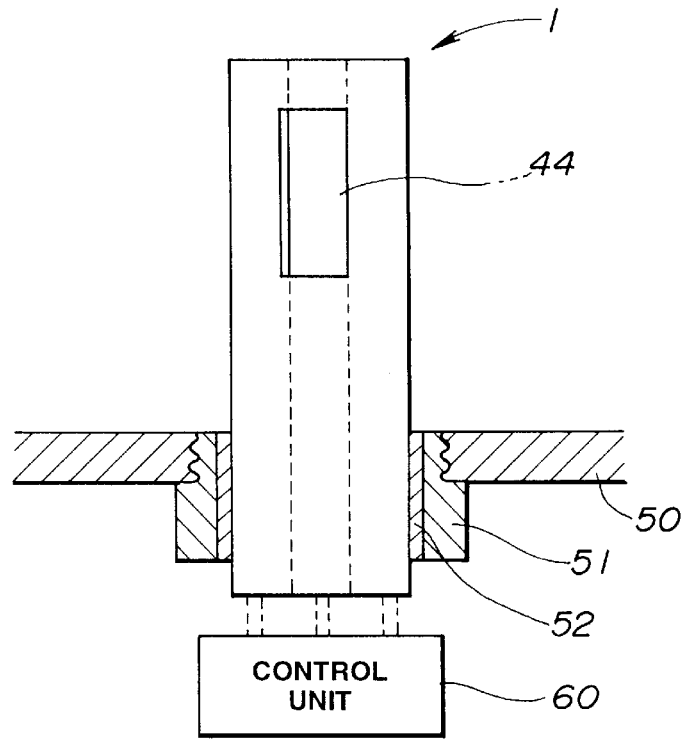
FIG. 14 is an illustration of how the exhaust gas sensor of FIG. 1 is installed on an exhaust pipe.

As shown in FIG. 14, the exhaust gas sensor 1 has a threaded portion 51 and an attachment portion 52 and is attached thereat to an exhaust pipe 50. In this instance, the porous electrodes 22 and 42 are connected to the control unit 60 which serves as an oxygen concentration control means by way of the lead portions 22a and 42a (refer to FIG. 1), respectively.

As shown in FIG. 2, exhaust gas EG is introduced into the detection space 44 by way of the porous ceramic member 46, so that the concentration of the harmful substances such as CO, HC or the like is detected by the semiconductor element 25. On the other hand, the concentration of oxygen in the exhaust gas EG is detected by the oxygen sensor cell 21.

A constant bias voltage VB is applied across the both Do porous electrodes 22 of the oxygen sensor cell 21 by means of a power source (not shown) provided within the control unit 60 in such a manner that the detection space 44 side goes negative and the reference gas introducing space side goes positive. Further, a pump voltage VP is applied across the both porous electrodes 42 of the oxygen pump cell 41 in such a direction as to cause oxygen to be conveyed or charged from the exhaust gas atmosphere side to the detection space 44 side or in such a direction as to cause oxygen to be conveyed or discharged out of the detection space 44. In the meantime, the heater unit 4 heats the oxygen sensor cell 21 and the oxygen pump cell 41 and hold them heated at a predetermined operating temperature (e.g., 300° C. or higher).

By the application of the Voltage VB, the oxygen contained in the exhaust gas EG is selectively conveyed to the reference gas introducing space side by means of the oxygen sensor cell 21. By this, the reference gas introducing space 24 is filled with oxygen gas of the oxygen concentration of nearly 100%, which oxygen gas is used as a reference gas. On the other hand, the exhaust gas EG within the detection space 44 is lower in the oxygen concentration than the above described reference gas, so there is caused a concentration cell electromotive force corresponding to the difference in the oxygen concentration therebetween and in such a direction as to cause current to flow from the reference gas introducing space to the detection space 44. The control unit 60 detects the concentration of oxygen in the exhaust gas on the basis of the output voltage VS of the oxygen sensor cell 21 to which the bias voltage VB is applied in addition to the concentration cell voltage and controls the pump voltage VP to be applied to the oxygen pump cell 41 in both directions so as to maintain the concentration of oxygen substantially constant. In the meantime, it is necessary to set the bias voltage VB to be larger than the concentration cell voltage generated in the oxygen sensor cell 21.

Figure 15:
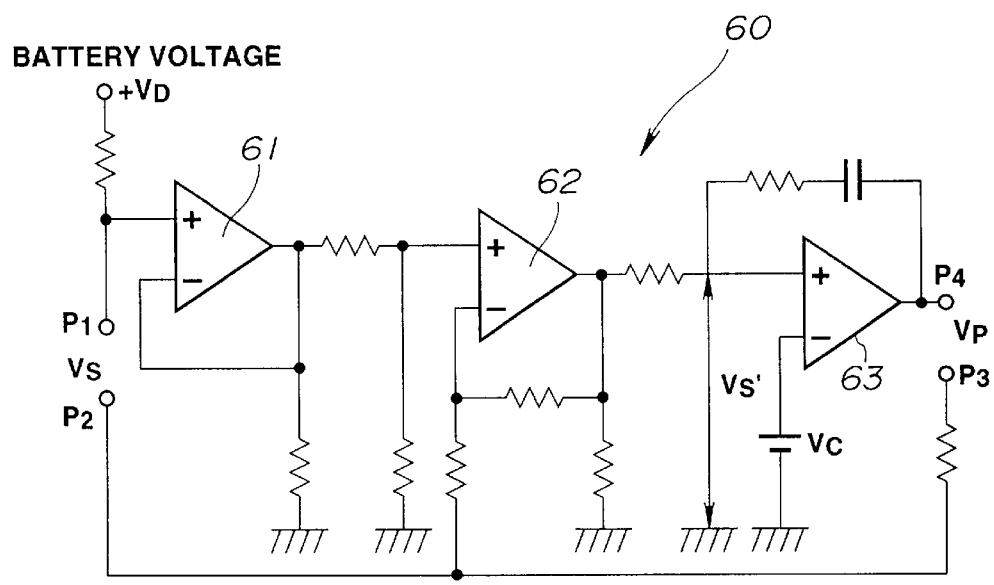
FIG. 15 is a circuit diagram of a control unit for the exhaust gas sensor of FIG. 1A.

FIG. 15 shows an example of a circuit for the control unit 60. The control unit 60 mainly consists of three operational amplifiers 61, 62 and 63, and the terminals P1 and P2 are connected with the respective electrodes 22 of the oxygen sensor cell 21 while the terminals P3 and P4 being connected with the respective electrodes 42 of the oxygen pump cell 41. The output voltage VS from the oxygen sensor cell 21 is amplified by a predetermined factor by means of the operational amplifiers 61 and 62 in the, preceding section and is thereafter compared with the reference voltage VC by means of the operational amplifier 63 in the succeeding section.

The operational amplifier 63 outputs the pump voltage VP proportional to the difference between the amplified input voltage VS' from the oxygen sensor cell 21 and the reference voltage VC. In this instance, in the case VS' is larger than VC, i.e., in the case the concentration QS of oxygen in the exhaust gas EG is smaller than the reference concentration QC that is determined in accordance with the reference voltage VC, the pump voltage VP is applied in such a direction as to make oxygen be conveyed into the detection space 44, while in the reverse case in such a direction as to make oxygen be conveyed out of the same. By this, the concentration of oxygen within the detection space is maintained substantially at a constant value adjacent the reference concentration QC. In the meantime, the control unit 60 can otherwise be constituted by using a microprocessor as a main component so as to carry out the above described control in accordance with a software.

By this, it becomes possible to solve the problem in that the detection output of the semiconductor detection element 25 varies depending upon a variation of the concentration of oxygen in exhaust gas and therefore it becomes possible to detect the concentration of contaminants in the exhaust gas with high accuracy. Further, since the porous electrodes 22 and 42 facing or associated with the detection space 44 are both made of Au which is small in catalytic activity about the reaction of the detected substance such as methane and the like with oxygen, consumption of the above described detected substance in the reaction with oxygen is prevented or restrained, thus similarly contributing to improvement in the accuracy in detection of the above described detected substance. Further, in the case the detection substance is methane, such an electrode has an excellent selectivity in the detection of it. In this instance, a particularly good selectivity in methane is obtained in case the operating temperature of exhaust gas sensor 1 is within the range from 650° C. to 800° C.

Figure 16:
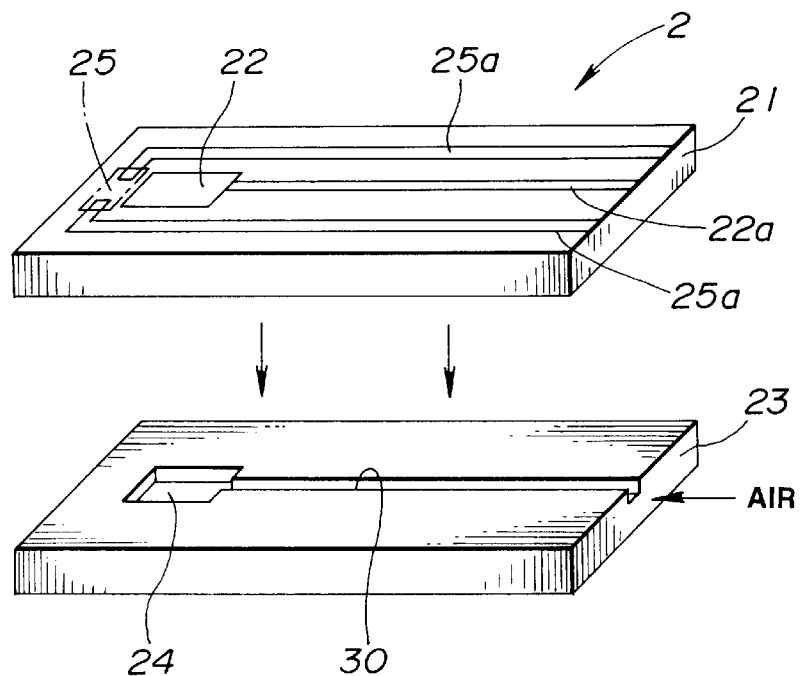
FIG. 16 is an exploded perspective view of a sensor cell unit having an open air communicated portion at a base member according to a further embodiment of the present invention.

In the meantime, in the case the reference gas introducing space is communicated with the open air, the control circuit may be structured so as not to apply the bias voltage VB to the oxygen sensor cell 21. Further, as shown in FIG. 16, the sensor cell unit 2 may be formed with an open air communicating portion 30 in the form of a groove for providing communication between the reference gas introducing space 24 and the open air. The open air communicating portion 30 is communicated at one end with the reference gas introducing space 24 and at the other end, which opens to an end face of the base member 23, with the open air.

Figure 17:
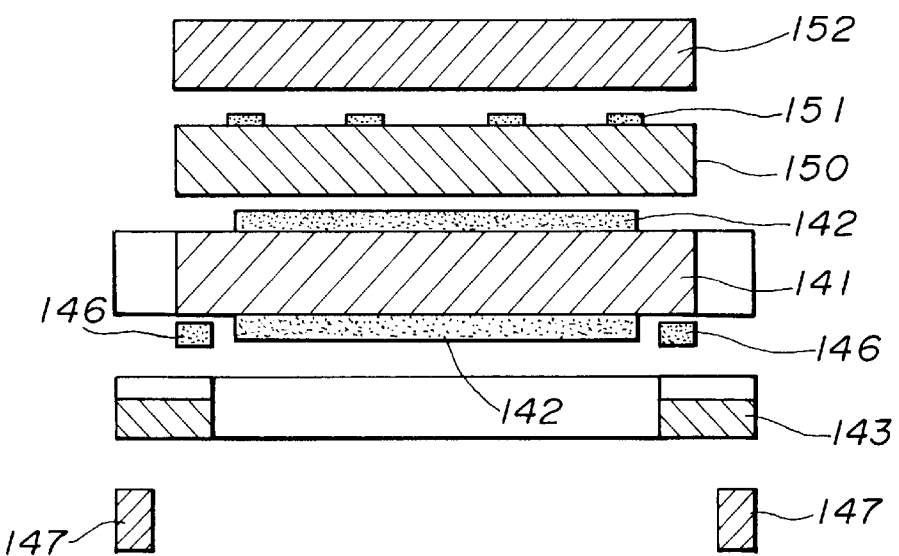
FIG. 17 is a schematic illustration of a process of firing a heater unit concurrently or simultaneously with firing of a pump cell unit.

Further, the heater unit 4 can be joined with the pump cell unit 3 by simultaneous or concurrent firing of them. That is, as shown in FIG. 17, on the surface of a powder compact 150 in the form of a plate, which is produced by compacting ceramic powder together with binder, a resistance heating wire pattern 151 is formed by printing of a paste including resistance heating material powder. On the surface on which the pattern 151 has been formed, another powder compact similarly in the form of plate is placed, and the laminated assembly is fired, whereby the exhaust gas sensor 1 with the heater unit 4 and the pump cell unit 3 joined to constitute an integral body or unit can be obtained. By this, the temperature control can be performed with higher accuracy, and the error in the output of the semiconductor detection element can be reduced to improve the reliability and the stability in operation of the exhaust gas sensor 1.

Figure 21A:
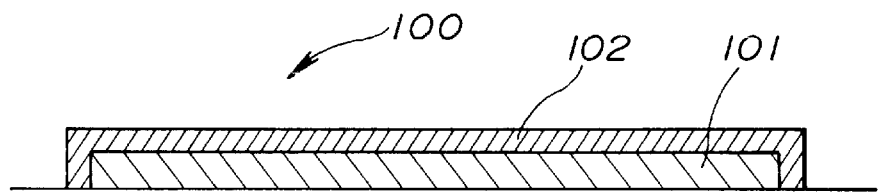
FIGS. 21A to 21C are illustrations of various examples of producing a catalytically inactive electrode by coating.

In the meantime, the porous electrodes 22 and 42 facing or associated with the detection space 44 can be made of Au alloy such as Au—Pd alloy or the like. Further, the electrodes can be made of Ag or Ag alloy such as Ag—Pd alloy. Otherwise, the electrodes can be made of such an alloy that is made lower in the catalytic activity of Pt by adding Au, Ni, Ag or the like metal to Pt. Further, as shown in FIG. 21A, it will do to form a porous electrode 100 by first forming a porous electrode main body 101 which is made of Pt, Rh, Pd, Ir or the like metal and then providing a coating 102 made of a catalytically inactive material such as Au base metal, Ag base metal, oxide such as $SnO_2$, $ZnO$, $In_2O_3$, $WO_3$, $Bi_2O_3$ or the like to the surface of the main body 101 for contact with exhaust gas.

Figure 21B:
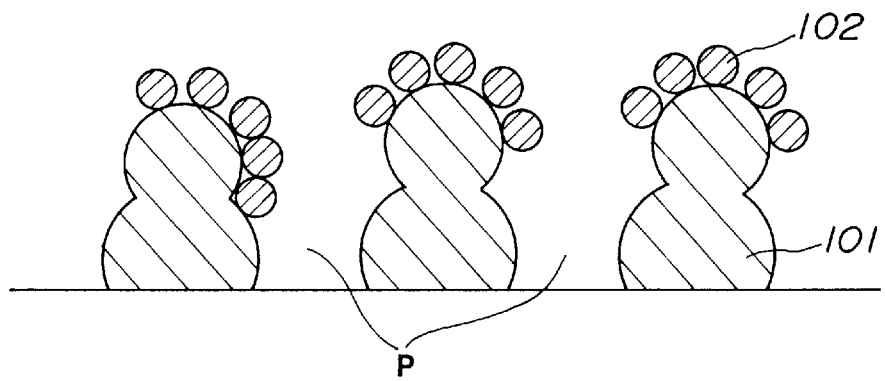
Figure 21C:
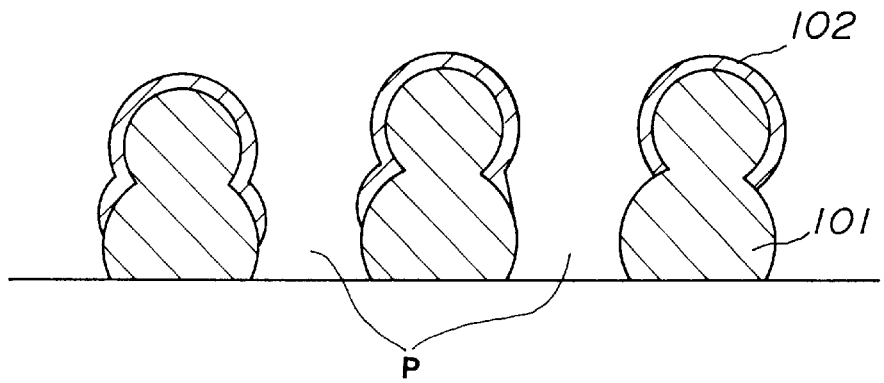

In this instance, the above described coating 102 may be formed by a method of applying a paste containing particles of the above described catalytically inactive material to the main body 101 and firing the paste secondarily as shown in FIG. 21B or by a vapor-phase film forming method such as vapor deposition, sputtering or the like as shown in FIGS. 21C. In the meantime, as schematically shown in FIGS. 21B and 21C, the porous main body 101 is formed so as to have a number of intricate pores P, so such a case may possibly occur in which the coating 102 is not formed so as to intrude deeply into the pores P. However, if the catalytic activity about the reaction of the detected substance and oxygen can be made sufficiently small, it does not matter that the electrode has such a portion not coated.

Further, in the case a detected substance other than methane is to be detected selectively, it will do that the porous electrode facing or associated with the detection space 44 is made of another material suited for detection of the detected substance or the operating temperature of the sensor is changed so as to be suited for selective detection of the substance desired to be detected. In the latter case, solid electrolyte suited for the operating temperature is used if necessary.

Hereinafter, the operation and effect of the exhaust gas sensor and exhaust gas sensor system according to the present invention will be described more in detail on the basis of test examples. An example of the exhaust gas sensor 1 shown in FIGS. 2A to 2C was produced according to the above described method. In this instance, it is determined that the solid electrolyte is $ZrO_2$ having a solid solution of $Y_2O_3$, the detection space 44 is 0.003 cm$^3$ in volume, each electrode 42 of the pump cell 41 is 0.08 cm$^2$ in area and 10 $\mu$m thick, and each electrode 22 of the oxygen sensor cell 21 is 0.02 cm$^2$ and 10 $\mu$m thick. In the meantime, it was also prepared a sensor in which all of the porous electrodes including those associated with the detection space 44, were made of Pt.

On the other hand, other than the above described sensors, examples in which a disk-shaped porous electrode of 8 mm in diameter and made of Au or Pt were prepared. The examples were disposed within a tubular receptacle having a gas inlet and outlet and heated up to 750° C. Under this condition, a test gas containing 300 ppm oxygen, 350 ppm methane and the remainder of Ar was charged through the inlet at the flow rate of 100 ml/min. and discharged through the outlet to measure the decrease percentage as to the concentration of methane in the test gas. As a result, in case of the example using the Pt porous electrode, the decrease percentage as to the concentration of oxygen reached 30%, so it was recognized that the catalytic activity for the reaction of methane and oxygen was large. In contrast to this, in case of the example using the Au porous electrode, the above described decrease percentage as to the concentration of methane was less than 10%, so it was confirmed that the example was catalytically inactive about the above reaction.

Then, the above described exhaust gas sensor was installed on the exhaust pipe and each terminals thereof were connected to the control unit shown in FIGS. 14 and 15. In this state, the exhaust gas sensor 1 was heated up to 750° C., and various measured gases consisting of various concentrations of oxygen in the range from 50 to 5000 ppm, various concentrations of detected substance in the range from 0 to 500 ppm and the remainder of nitrogen were conducted through the exhaust pipe at the flow rate of 12 l/min. to measure the resistance of the semiconductor element. In the meantime, selected as the detected substance is either of methane ($CH_4$), propylene ($C_3H_6$), carbon monoxide (CO) or nitrogen monoxide (NO).

Figure 18A:
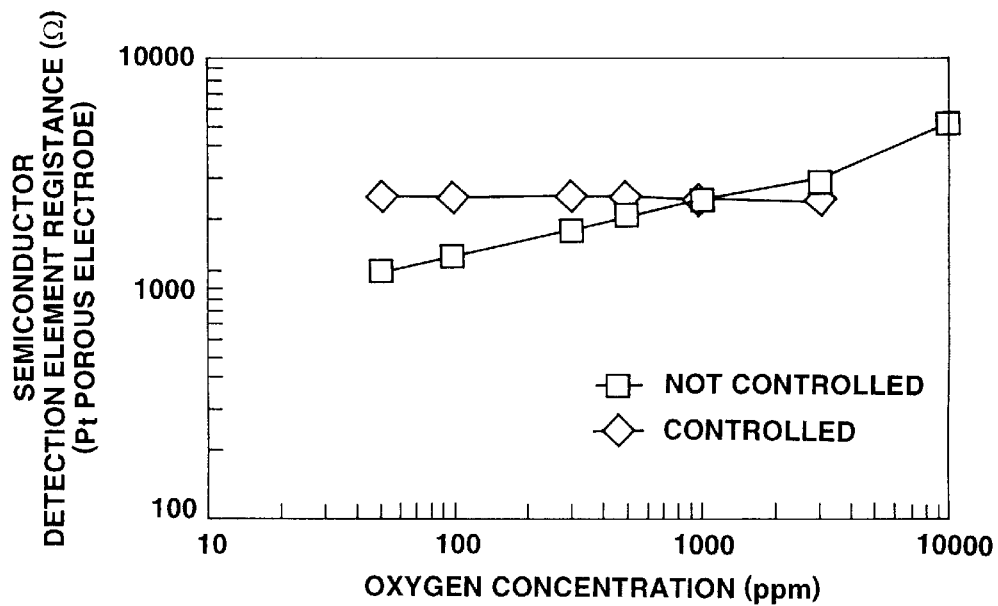
FIGS. 18A and 18B are graphs of a relation between resistance of semiconductor detection element and oxygen concentration, obtained by the respective embodiments of the present invention.
Figure 18B:
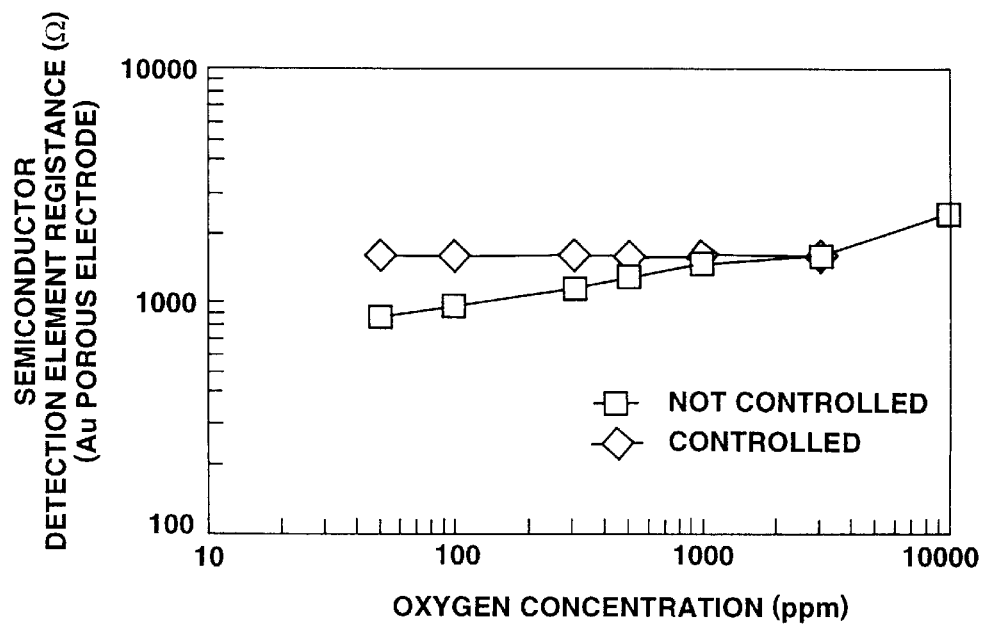

FIGS. 18A and 18B are the graphs showing the detection result of the resistance of the semiconductor element 25 in relation to the concentration of oxygen in the measured or tested gas, resulting when the concentration of oxygen is varied variously within the above described range, with respect to the cases the concentration of oxygen in the detection space 44 is controlled or not. In the meantime, FIG. 18A shows the result obtained when Pt porous electrodes were used for the electrodes 22 and 42 on the detection space 44 side, and FIG. 18B shows the result obtained when Au porous electrodes were used. In either case of Pt or Au porous electrodes, the resistance of the semiconductor detection element 25 varies depending upon a variation of the concentration of oxygen in the test gas when the control by the control unit 60 is not carried out, whereas when the control is carried out, the resistance becomes substantially constant, so it is seen that the concentration of oxygen in the detection space 44 is maintained substantially constant. Further, it is indicated or meant by this that both of the Pt porous electrode and Au porous electrode have an excellent oxygen dissociating and catalyzing function.

Figure 19A:
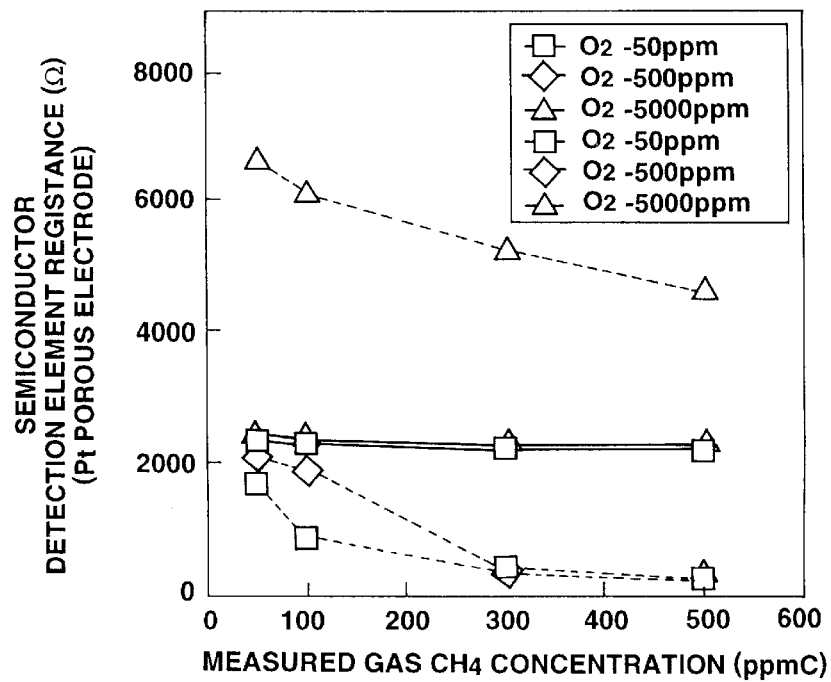
FIGS. 19A and 19B are graphs of a relation between resistance of semiconductor detection element and concentration of measured gas $CH_4$, obtained by the respective embodiments of the present invention.
Figure 19B:
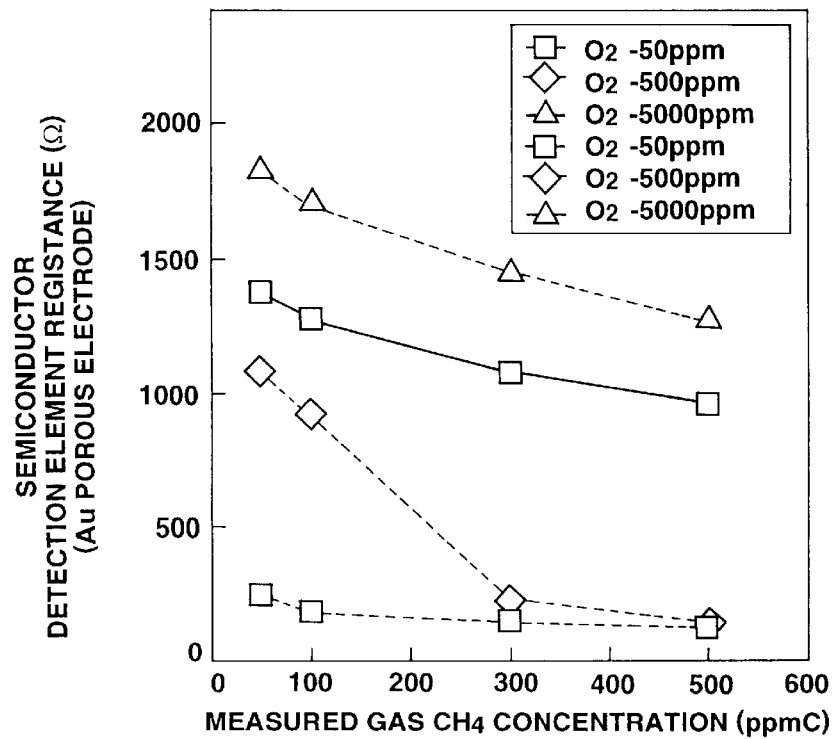

FIGS. 19A and 19B are graphs in which the detection result of the resistance of the semiconductor detection element 25 resulting when both of the methane concentration and oxygen concentration are varied variously within the above described range, is represented by lines for each oxygen concentrations in relation to the concentration of methane in the measured or tested gas and with respect to the cases the concentration of oxygen in the detection space 44 is controlled or not. In the meantime, FIGS. 19A shows the result obtained when Pt porous electrodes are used for the electrodes 22 and 42 on the detection space 44 side, and FIG. 19B shows the result obtained when Au porous electrodes are used. Further, the solid lines in the graphs represent the case where the control is made on the concentration of oxygen in the detection space 44 according to the present invention, whereas the dotted lines represent the case where the control is not made.

That is, as seen from the graph of FIG. 19A, although the resistance of the semiconductor detection element 25, when Pt porous electrodes are used for the detection space 44 side electrodes 22 and 42, is scarcely influenced by a variation of the concentration of oxygen in measured gas by the effect of the oxygen concentration control, its variation in response to a variation of the methane concentration is also small, so it will be seen that improvement in the accuracy in detection of methane cannot be expected too much. On the other hand, as shown in FIG. 19B, in the case the Au porous electrodes are used, the resistance of the semiconductor detection element 25 reduces nearly rectilinearly, so it is seen that a good detection characteristic is exhibited. Further, in the graph of FIG. 19B, though only one solid line representative of the oxygen concentration of 50 ppm is shown, three solid lines representative of the oxygen concentrations of 50 ppm, 500 ppm and 5000 ppm are actually superimposed one upon another. This shows that the measurement lines for each oxygen concentrations coincide approximately with each other, so it is seen that a stable sensor output can be obtained even when a variation in the concentration of oxygen in the detected gas occurs.

Figure 20:
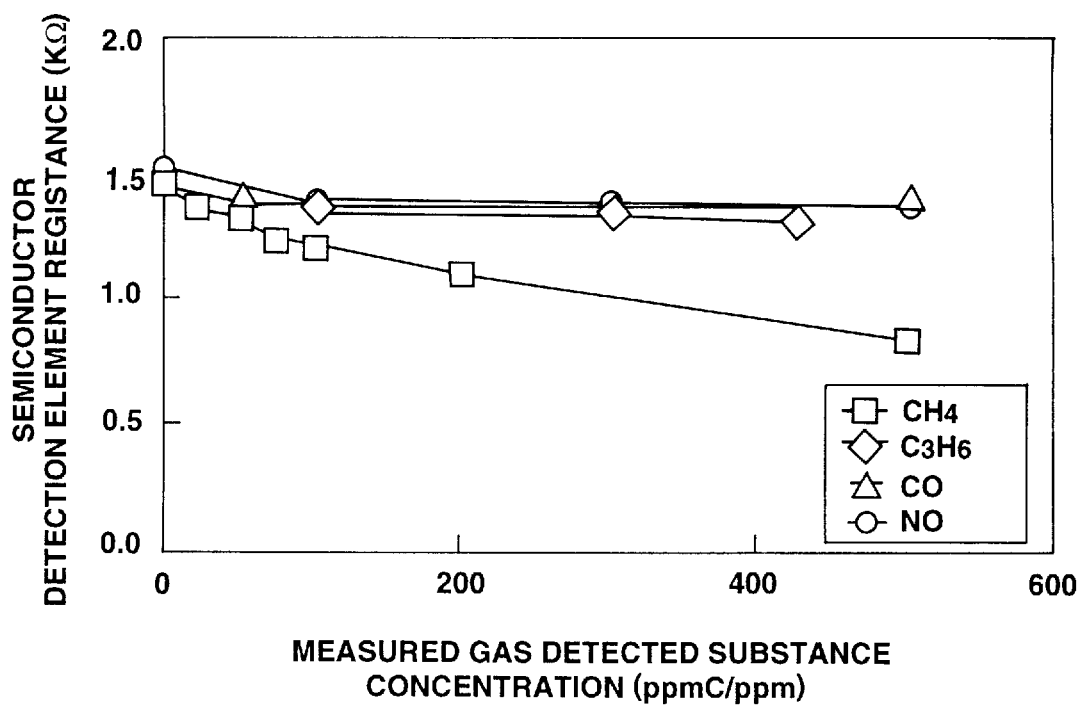
FIG. 20 is a graph of a relation between resistance of semiconductor detection element and concentrations of various measured gas detected substances.

FIG. 20 is a graph showing the resistance of the semiconductor element 25 in relation to the concentration of various detected substance when the Au porous electrodes are used in the sensor and the measured gas is changed variously. From the graph, it is seen that the resistance of the semiconductor element 25 in the sensor varies largely in case the detected substance is methane, so the sensor is excellent in the selectivity of detection of methane.

What is claimed is:

1. An exhaust gas sensor comprising:
    a pump cell unit having an oxygen pump cell made of oxygen-ion conductive solid electrolyte and a pair of porous electrodes formed thereon, for charging or discharging oxygen into or from a detection space;
    a sensor cell unit including an oxygen sensor cell made of oxygen-ion conductive solid electrolyte and a pair of porous electrodes formed thereon, and disposed opposite to said oxygen pump cell to define therebetween said detection space, for detecting the concentration of oxygen in an exhaust gas introduced into said detection space on the basis of a concentration cell electromotive force resulting from the difference in concentration of oxygen between the exhaust gas in said detection space and a reference gas;
    said pump cell unit controlling charge or discharge of oxygen into or from said detection space on the basis of concentration of oxygen in the exhaust gas, which is detected by said sensor cell unit, so that the concentration of oxygen in said detection space is regulated to a predetermined value; and
    a semiconductor detection element made of an oxide of a semiconductor and disposed in said detection space for detecting a predetermined substance in the exhaust gas in said detection space, wherein one of said electrodes of said pump cell unit and one of said electrodes of said sensor cell unit are exposed to said detection space and each include a porous main body made of metal selected from a group consisting of Pt, Rh, Pd and Ir, and a coating formed on said main body and made of a catalytically inactive material selected from a group consisting of Au base alloy, Ag base alloy, $SnO_2$, ZnO, $In_3O_3$, $WO_3$ and $Bi_2O_3$.

2. An exhaust gas sensor according to claim 1, wherein said semiconductor detection element is disposed on said oxygen sensor cell with an insulation layer interposed therebetween and at a location adjacent said electrodes of said oxygen sensor cell unit.

3. An exhaust gas sensor according to claim 1, wherein said semiconductor detection element is of a sintered kind formed by printing a predetermined element pattern on said oxygen sensor cell which is previously sintered, by using starting material powder of said oxide semiconductor, and thereafter by secondarily sintering said printed pattern at a temperature lower than a sintering temperature of said oxygen sensor cell.

4. An exhaust gas sensor according to claim 1, wherein said pump cell unit has a coupling portion, said sensor cell unit has a coupling portion, and said pump cell unit and said sensor cell unit are joined together at said coupling portions with adhesive.

5. An exhaust gas sensor according to claim 1, wherein said pump cell unit includes,
    said oxygen pump cell formed into an elongated plate shape,
    a detection space forming member formed into a plate shape corresponding to that of said oxygen pump cell and formed with a window portion penetrating therethrough in the thickness direction for forming said detection space, and
    a pair of coupling projections disposed on the side of said detection space forming member opposite to said oxygen pump cell and formed integral with and along opposite ends of said detection space forming member opposed widthwise thereof, wherein said sensor cell unit includes, said oxygen sensor cell in the form of an elongated plate narrower than said detection space forming member, and a base member formed wider than said oxygen sensor cell and placed on a side surface of said oxygen sensor cell opposite to said detection space forming member in such a manner as to have opposite end portions protruding widthwise from said oxygen sensor cell, said protruded opposite end portions of said base member and said oxygen sensor cell constituting a stepped surface, wherein said pump cell unit and said sensor cell unit being placed one upon another and joined together to constitute an integral body, with said coupling projections of said pump cell unit being coupled with said stepped surface, and wherein said coupling projections and said stepped surface constituting said coupling portions of said pump cell unit and said sensor cell unit, respectively.

6. An exhaust gas sensor according to claim 1, wherein said electrodes of said pump cell unit and said sensor cell unit exposed to said detection space are catalytically inactive in a reaction of said predetermined substance in the exhaust gas and oxygen.

7. An exhaust gas sensor according to claim 1, wherein said predetermined substance is methane.

8. The exhaust gas sensor according to claim 1, wherein said oxygen pump cell is in the form of a rectangular plate and has at each of opposite sides thereof a joining portion of a rectangular cross section and said oxygen sensor cell has at each of opposite sides thereof a joining portion of a rectangular cross section on which said joining portion of said oxygen pump cell is fitted to define therebetween a clearance which is cranked in cross section to have a pair of horizontal clearance sections and a vertical clearance section interconnecting said horizontal clearance sections and in which an adhesive is filled, said joining, portion of said oxygen pump cell and said joining portion of said oxygen sensor cell being chamfered at corners thereof so that said clearance is partially increased to provide adhesive collecting portions.

9. The exhaust gas sensor according to claim 8, wherein said joining portion of said oxygen pump cell is in the form of protrusions and said joining portion of said oxygen sensor cell is in the form of depressions.

* * * * *